United States Patent
Jabes et al.

(10) Patent No.: US 7,317,001 B2
(45) Date of Patent: Jan. 8, 2008

(54) USE OF RAMOPLANIN TO TREAT DISEASES ASSOCIATED WITH THE USE OF ANTIBIOTICS

(75) Inventors: Daniela Jabes, Cassina Rizzardi (IT); Timothy S. Leach, Groton, MA (US); Richard F. Labaudiniere, Sherborn, MA (US); Steven M. Rauscher, Lexington, MA (US); Giorgio Mosconi, Wayne, PA (US)

(73) Assignee: Oscient Pharmaceuticals Corporation, Waltham, MA (US)

( * ) Notice: Subject to any disclaimer, the term of this patent is extended or adjusted under 35 U.S.C. 154(b) by 565 days.

(21) Appl. No.: 10/454,998

(22) Filed: Jun. 5, 2003

(65) Prior Publication Data

US 2004/0072732 A1    Apr. 15, 2004

Related U.S. Application Data

(60) Provisional application No. 60/385,902, filed on Jun. 6, 2002, provisional application No. 60/469,803, filed on May 12, 2003.

(51) Int. Cl.
*A61K 38/00* (2006.01)
(52) U.S. Cl. .................................................. 514/11
(58) Field of Classification Search ................. 514/11
See application file for complete search history.

(56) References Cited

U.S. PATENT DOCUMENTS 4,303,646 A * 12/1981 Cavalleri et al. ............ 424/118
4,328,316 A    5/1982 Cavalleri et al. ............ 435/253
4,427,656 A    1/1984 Cavalleri et al. ............ 424/118
5,108,988 A    4/1992 Ciabatti et al. ............... 514/11
5,491,128 A    2/1996 Ciabatti et al. ............... 514/11
5,539,087 A    7/1996 Restelli et al. .............. 530/412
5,752,941 A    5/1998 Romano' et al. ............ 604/265
5,925,550 A    7/1999 Lancini et al. ............. 435/71.3

FOREIGN PATENT DOCUMENTS

| WO | WO 99/30690 | 6/1999 |
| WO | WO 01/44271 A2 | 6/2001 |
| WO | WO 01/44272 A2 | 6/2001 |
| WO | WO 01/44274 A2 | 6/2001 |
| WO | WO 01/53330 A2 | 7/2001 |
| WO | WO 01/70213 A2 | 9/2001 |
| WO | WO 01/97851 A2 | 12/2001 |

(Continued)

OTHER PUBLICATIONS

Biavasco et al., Antimicrobial Agents and Chemotherapy, 1991; 35(1): 195-197.*

(Continued)

*Primary Examiner*—San-ming Hui
(74) *Attorney, Agent, or Firm*—Hamilton, Brook, Smith & Reynolds, P.C.

(57) ABSTRACT

The invention features a method of treating or preventing a disease associated with the use of antibiotics in a patient in need thereof by administering to the patient ramoplanin in an amount and for a duration effective to treat said disease. The disease may be caused, for example, by the presence of a bacterium such as enterotoxin producing strains of *C. difficile*, *C. perfringens*, or *S. aureus*.

8 Claims, 5 Drawing Sheets

Experimental conditions: clindamycin induced CdAD
Effect of Ramoplanin or Vancomycin

FOREIGN PATENT DOCUMENTS

| | | |
|---|---|---|
| WO | WO 02/05838 A1 | 1/2002 |
| WO | WO 02/15959 A2 | 2/2002 |
| WO | WO 02/056829 A2 | 7/2002 |
| WO | WO 02/059145 A1 | 8/2002 |
| WO | WO 02/059322 A2 | 8/2002 |

OTHER PUBLICATIONS

Baden et al., "Molecular characterization of vancomycin-resistant enterococci repopulating the gastrointestinal tract following treatment with a novel glycolipodepsipeptide, ramoplanin," *J. Clinical Microbiol.*, 40:1160-1163 (2002).

Bartoloni et al., "Comparative in vitro activity of MDL 62211 against gram-positive bacteria," 29th *Interscience Conference on Antimicrobial Agents and Chemotherapy*, Abstract (1989).

Bartoloni et al., "In-vitro activity of vancomycin, teicoplanin, daptomycin, ramoplanin, MDL 62873 and other agents against *staphylococci, enterococci* and *Clostridium difficile,*" *J. Antimicrobial Chomotherapy* 26:627-633 (1990).

Bartoloni et al., "In vitro activity of MDL 62,879 against gram-positive bacteria and bacteroides species," *Eur. J. Clin. Microbiol. Infect. Dis.* 14:1105-108 (1995).

Bartoloni et al., "In vitro activity of MDL 62,879 against *Clostridium difficile, Propionibacterium acnes, Bacteroides fragilis* and *Bacteroides* spp.," *Interscience Conference on Antimicrobial Agents and Chemotherapy* (Abstract F-117) 1995.

Citron et al., "In vitro activities of ramoplanin, teicoplanin, vancomycin, linezolid, bacitracin, and four other antimicrobials against intestinal anaerobic bacteria," *Antimicrobial Agents and Chemotherapy* 47:2334-2338 (2003).

Fekety et al., "In vitro susceptibility of *Clostridium difficile* to Ramoplanin R.," 32nd *Interscience Conference on Antimicrobial Agents and Chemotherapy* (Abstract 490) 1992.

Hassan et al., "In vitro activity of teicoplanin, vancomycin, A16686, clindamycin, erythromycin and fusidic acid against anaerobic bacteria," *Singapore Med. J.* 31:56-58 (1990).

Jabes et al., "Superior efficacy of short treatment duration of ramoplanin over vancomycin in the hamster model of *C. difficile* associated colitis," 43rd *American Society for Microbiology* (Abstract B-328) 2003.

Neu et al., "In vitro activity of A-16686, a new glycopeptide," *Chemotherapy* 32:453-457 (1986).

O'Hare et al., "In vitro activity of A-16686—A novel glycopeptide active against gram positive bacteria," 15th *International Congress of Chemotherapy*, (Abstract 390) 1987.

O'Hare et al., "In-vitro studies with ramoplanin (MDL 62, 198): a novel lipoglycopeptide antimicrobial," *J. Antimicrobial Chemotherapy* 25:217-220 (1990).

Peláez et al. "In vitro activity of ramoplanin against *Clostridium difficile*, including strains with reduced susceptibility to vancomycin or with resistance to metronidazole," 43rd *Interscience Conference on Antimicrobial Agents and Chemotherapy* (Abstract E-2188) 2003.

Ravizzola et al., "Attivita' antibatterica di un nuovo glicopeptide A-16686 nei confronti di microorganismi gram-positivi," *Biol. Microbial. Lab* 4:51-56 (1987). (English abstract).

Ravizzola et al., A-16686, a new glycopeptide: in vitro evaluation in comparison with other antibiotics, *J. Chemother.* 1(Suppl. 4):212-213 (1989).

Romano et al., Bactericidal activity of ramoplanin (RA) against *Clostridium* sp. 41st *Interscience Conference on Antimicrobial Agents and Chemotherapy* (Abstract E-2260) 2001.

Wilcox et al., "Surveillance for resistance to metronidazole, vancomycin or ramoplanin in genotypically distinct and clonal *Clostridium difficile* strains," 43rd *Interscience Conference on Antimicrobial Agents and Chemotherapy* (Abstract E-2190) 2003.

Wong et al., "Effective suppression of vancomycin-resistant *Enterocuss* species in asymptomatic gastrointestinal carriers by a novel glycolipodepsipeptide, ramoplanin," *Clin. Infect. Dis.* 33:1476-1482 (2001).

Bartlett, "Treatment of antibiotic-associated pseudomembranous colitis," *Reviews of Infectious Diseases* 6(Suppl 1):S235-S241 (1984).

Biavasco et al., "In vitro activities of ramoplanin and four glycopeptide antibiotics against clinical isolates of *Clostridium difficile,*" *Antimicrobial Agents and Chemotherapy* 35:195-197 (1991).

Dworczynski et al., "Susceptibility of *Clostridium difficile* Strains o Teicoplanin and Ramoplanin," *Otrzymano* 7:486 (1993).

Romeo et al., "Repeated Doses of Ramoplanin Orally Administered to Healthy Male Volunteers: Tolerability, Lack of Absorption and Effect on the Stool Microflora," Abstract No. 448, Session 40, *Abstracts of the 33rd ICAAC* (1993).

de Lalla et al., "Oral Ramoplanin (R) Single-Dose Administration in Pseudomembranous Colitis (PMC)," Abstract No. 4102, *Can. J. Infect. Dis.* 6 (suppl. C):4526 (1995).

Bowie, W.R., et al., "Failure of Norfloxacin to Eradicate *Chlamydia trachomatis* in Nongonococcal Urethritis," *Antimicrobial Agents and Chemotherapy* 30(4):594-597 (1986).

Silverman, J.A., et al., "Inhibition of Daptomycin by Pulmonary Surfactant: In Vitro Modeling and Clinical Impact," *Journal of Infectious Diseases* 191:2149-2152 (2005).

Mégraud, F., et al., "Bactericidal Effect of Amoxicillin on *Helicobacter pylori* in an In Vitro Model Using Epithelial Cells," *Antimicrobial Agents and Chemotherapy* 35(5):869-872 (1991).

McFarland, L.V., "Alternative Treatments for *Clostridium difficile* Disease: What Really Works?" *Journal of Medical Microbiology* 54:101-111 (2005).

Declaration of Daniela Jabes, Ph.D. Under 37 C.F.R. § 1.132, dated Apr. 30, 2007.

Declaration Pursuant to 37 C.F.R. § 1.132 by Thomas S. Leach Dated Jun. 14, 2007.

* cited by examiner

Experimental conditions: clindamycin + C. Diff 4013 induced CdAD
Effect of Ramoplanin

Experimental conditions: clindamycin + C.diff induced CdAD Effect of different treatment durations of Vancomycin and Ramoplanin

Hamsters were inoculated with C. difficile CD 4013 on day 0 and challenged with 100 mg/kg of clindamycin sc on day 1. Hamsters received daily doses of 50 mg/kg of Ramoplanin or Vancomycin for 3 or 5 days orally starting on day 2

USE OF RAMOPLANIN TO TREAT DISEASES ASSOCIATED WITH THE USE OF ANTIBIOTICS

CROSS-REFERENCE TO RELATED APPLICATIONS

This application claims benefit of U.S. Provisional Application Nos. 60/385,902 (filed Jun. 6, 2002) and 60/469,803 (filed May 12, 2003), each of which is hereby incorporated by reference.

FIELD OF THE INVENTION

This invention relates to the treatment of diseases associated with the use of antibiotics, such as colitis, pseudomembranous colitis, and antibiotic associated diarrhea.

BACKGROUND OF THE INVENTION

Antibiotic-associated diarrheal diseases are caused by enterotoxin producing strains of Clostridium difficile, Staphylococcus aureus and Clostridium perfringens, and represent a major economic burden to the healthcare system, that is conservatively estimated at $3-6 billion per year in excess hospital costs in the U.S. alone.

Clostridium difficile associated diarrhea (CDAD) is the most common cause of infectious, hospital-acquired diarrhea in the United States, and its incidence is increasing. With some estimates of its incidence as high as 3 million cases/year, it is clearly a major nosocomial infectious disease. The illness is caused by Clostridium (C.) difficile, an anaerobic, spore forming, Gram-positive bacterium that produces two enterotoxins (A and B). The spectrum of CDAD may range from mild, self-limited diarrhea to fulminant, life-threatening pseudomembranous colitis.

The two most important risk factors for CDAD are recent exposure to an antibiotic and exposure to a toxin-producing strain of the organism. Patients treated with clindamycin appear to be highly susceptible to CDAD presumably due to its prolonged effects on the indigenous anaerobic bowel flora. Host susceptibility also appears to be a critical factor in the development of CDAD since asymptomatic colonization is the most common outcome after exposure to the organism. Indeed, a recent report suggests that increased serum levels of immunoglobulin G against toxin A are associated with asymptomatic carriage of the organism post-exposure.

There are currently two dominant therapies for CDAD: vancomycin and metronidazole. While only vancomycin is approved by the Food and Drug Administration (FDA) for this indication, metronidazole is recommended as initial therapy out of concern for the promotion and selection of vancomycin resistant gut flora, especially enterococci. Oral bacitracin has also been used for the treatment of CDAD, although very infrequently. Recently there have been reports of C. difficile tolerance or resistance to vancomycin and metronidazole (Pelaez et al., Antimicrob. Agents Chemother. 46:1617-1618, 2002; Pelaez et al., Antimicrob. Agents Chemother. 46:1647-1650, 2002). While both vancomycin and metronidazole are generally very well tolerated and effective, allergies, intolerances, and side effects to both agents do occur.

Broad spectrum, anti-anaerobic agents such as metronidazole have also been shown to increase the density of vancomycin-resistant enterococcus (VRE) in the stool of colonized patients, and patients with CDAD may be at greater risk for VRE bacteremia in some populations. Given the limited therapeutic alternatives for the treatment of CDAD, and incipient reports of resistance, new therapies are needed.

SUMMARY OF THE INVENTION

The present invention relates to the treatment and prevention of antibiotic associated conditions such as colitis, pseudomembranous colitis, and antibiotic associated diarrhea by the administration of ramoplanin. Treatment with ramoplanin can be performed without increasing the concentration of vancomycin resistant enterococci (VRE) in the gut.

In one aspect, the invention features a method of treating or preventing a disease associated with the use of antibiotics in a patient in need thereof by administering to the patient ramoplanin in an amount and for a duration effective to treat said disease. The disease may be caused, for example, by the presence of a bacterium such as enterotoxin producing strains of C. difficile, C. perfringens, or Staphylococcus (S.) aureus. Exemplary diseases are antibiotic-associated diarrhea, colitis, and pseudomembranous colitis.

In a related aspect, the invention features a method of inhibiting onset of an antibiotic-associated condition in a patient in need thereof by administering to the patient ramoplanin in an amount and for a duration sufficient to inhibit onset of the antibiotic-associated condition. The antibiotic-associated condition may be antibiotic-associated diarrhea, colitis, or pseudomembranous colitis, or may be another disease caused by the presence of toxigenic C. difficile, S. aureus, or C. perfringens.

In another related aspect, the invention features a method of inhibiting relapse of antibiotic-associated diarrhea in a patient by administering ramoplanin in an amount and for a duration effective to inhibit relapse of antibiotic-associated diarrhea in the patient.

The invention also features a method of treating a disease caused by a bacterial infection of the colon (e.g., antibiotic-associated diarrhea or pseudomembranous colitis) by administering to a patient in need thereof an effective amount of ramoplanin in a pharmaceutical formulation that permits release of the ramoplanin into the patient's gastrointestinal tract. This pharmaceutical formulation can treat gastrointestinal infections caused by toxigenic strains of C. difficile, S. aureus, and C. perfringens.

The invention also features a method for preventing sporulation of C. difficile in a patient in need thereof by administering to the patient ramoplanin in an amount and for a duration effective to prevent sporulation of C. difficile.

In any of the foregoing methods, ramoplanin is typically administered in an amount between 50 mg and 1 g, although higher or lower doses may be required. Administration may be daily (e.g., one to four times daily) or may be less frequent (e.g., once every other day or once or twice weekly). In a desired embodiment, ramoplanin is administered in an amount between 100 and 400 mg once or twice daily. While the duration of ramoplanin therapy is determined on a case-by-case basis, typically administration is for three to fifteen days. Treatment durations shorter than standard therapies may be warranted with ramoplanin. Oral administration is preferred.

The ramoplanin administration may be performed in conjunction with other therapies. For example, the patient may also receive a second antibiotic (e.g., vancomycin, bacitracin, or metronidazole) or an antidiarrheal preparation (e.g., bismuth, diphenoxylate, atropine, kaolin, pectin, loperamide, or paragoric). Ramoplanin may be co-formulated with any of the foregoing, or may be administered separately.

Ramoplanin may also be formulated or used with corticosteroids. Corticosteroids include algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, amcinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methylprednisolone, methylprednisolone acetate, methylprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21 (beta-D-glucuronide), prednisone, prednylidene, procinonide, tralonide, triamcinolone, triamcinolone acetonide, triameinolone acetonide 21-palmitate, triamcinolone diacetate, and triamcinolone hexacetonide. Desirably, the corticosteroid is selected from budesonide, cortisone, dexamethasone, hydrocortisone, methylprenisolone, prednisone, triamcinolone, and diflorasone.

Ramoplanin may also be formulated or used with non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate), DMARDs, i.e., disease modifying antirheumatic drugs (e.g., cyclosporine, azathioprine, methotrexate, leflunomide, cyclophosphamide, hydroxychloroquine, sulfasalazine, D-penicillamine, minocycline, and gold), recombinant proteins (e.g., ENBREL® (etanercept, a soluble TNF receptor) and REMICADE® (infliximab) a chimeric monoclonal anti-TNF antibody), 5-ASA (mesalamine) drugs (e.g., sulfasalazine, olsalazine, balsalazide), azathioprine, 6-mercaptopurine, and methotrexate.

Ramoplanin and one or more of the foregoing compounds can be packaged as components of a kit (e.g., as a single pharmaceutical composition), which optionally also includes instructions for administering the two agents to a patient diagnosed as having a disease caused by a bacterial infection of the colon. The two compounds are desirably administered within 10 days of each other, within five days of each other, or within twenty-four hours of each other. In certain embodiments, the two compounds are administered simultaneously.

By "antibiotic-associated condition" is meant a condition resulting when antibiotic therapy disturbs the balance of the microbial flora of the gut, allowing pathogenic organisms such as enterotoxin producing strains of *C. difficile, S. aureus* and *C. perfringens* to flourish. These organisms can cause diarrhea, pseudomembranous colitis, and colitis and are manifested by diarrhea, urgency, abdominal cramps, tenesmus, fever among other symptoms. Diarrhea, when severe, causes dehydration and the medical complications associated with dehydration.

By "pseudomembranous colitis" or "enteritis" is meant an inflammation of the mucous membrane of both the small and large intestine with the formation of pseudomembranous material (i.e., material composed of fibrin, mucous, necrotic epithelial cells and leukocytes).

By "ramoplanin" is meant A/16686 or a preparation containing approximately 80% (with respect to the whole antibiotic substance, by HPLC assay) of A2 of A/16686 with a range of between 50-100%. The remaining portions consist essentially of small amounts of the related A and A' factors of A/16686. Preparations of this type are currently obtained from pilot or semi-industrial fermentation and recovery operations described in detail in U.S. Pat. No. 4,303,646.

By "patient" is meant a human in need of medical treatment. For the purposes of this invention, patients are typically institutionalized in a primary medical care facility such as a hospital or nursing home. However, treatment of a disease associated with the use of antibiotics can occur on an outpatient basis, upon discharge from a primary care facility, or can be prescribed by a physician for home-care, not in association with a primary medical care facility.

By "corticosteroid" is meant any naturally occurring or synthetic steroid hormone that can be derived from cholesterol and is characterized by a hydrogenated cyclopentanoperhydrophenanthrene ring system. Naturally occurring corticosteriods are generally produced by the adrenal cortex. Synthetic corticosteriods may be halogenated. Functional groups required for activity include a double bond at 4, a C3 ketone, and a C20 ketone. Corticosteroids may have glucocorticoid and/or mineralocorticoid activity. Examples of exemplary corticosteroids are described above.

The treatment of the present invention allows for the effective treatment of diarrheal diseases associated with enterotoxigenic strains of *C. difficile, S. aureus*, and *C. perfringens* without compromising systemic antibiotics and without increasing vancomycin resistant enterococci (VRE) in the gut. The present invention also reduces the presence of VRE in the gut. Other features and advantages will be apparent from the description

DETAILED DESCRIPTION OF THE INVENTION

Figure 1:
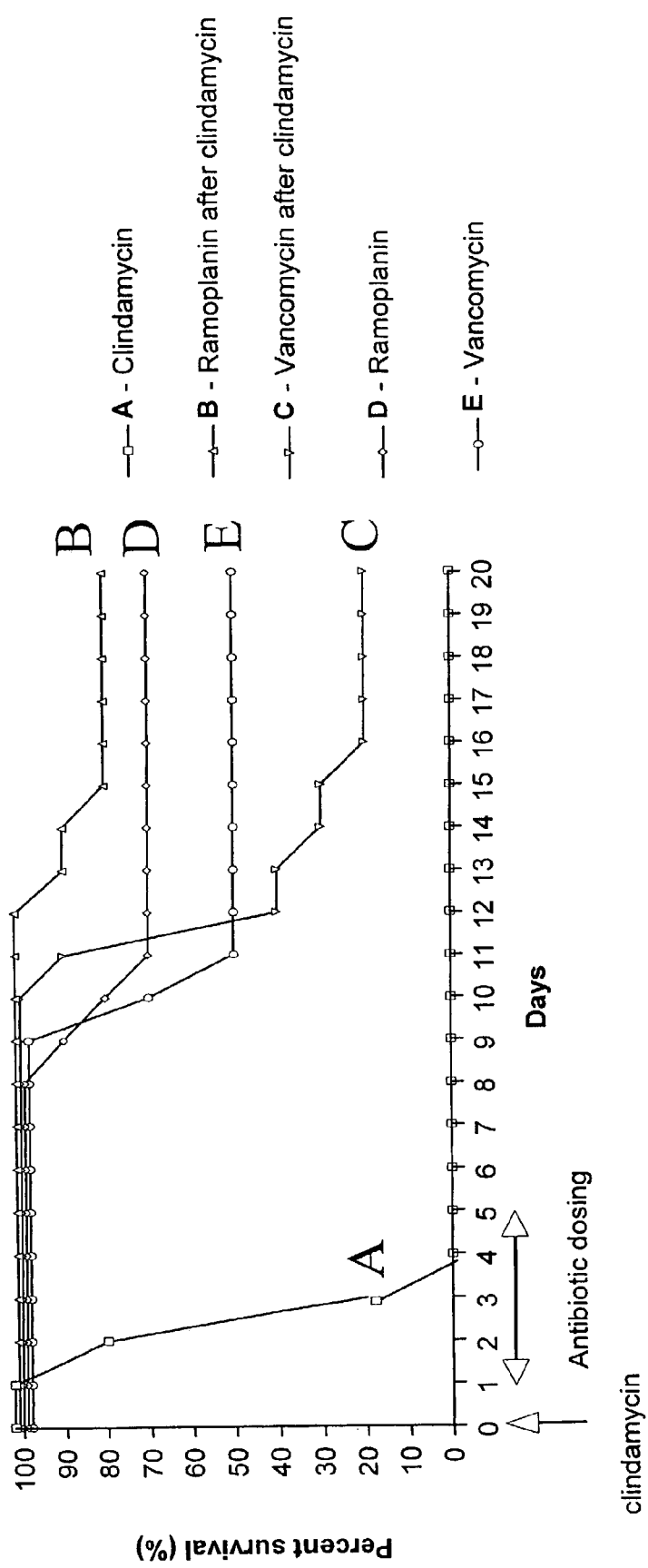
FIG. 1 is a graph showing the effect of ramoplanin or vancomycin on clindamycin-induced CDAD in Syrian hamsters.

The present invention relates to the unexpected discovery that conditions associated with the use of antibiotics, such as diarrhea associated with *C. difficile, S. aureus*, or *C. perfringens*, can be treated or prevented by the administration of ramoplanin in patients. The subject antibiotic-associated conditions include, but are not limited to, antibiotic-associated diarrhea, colitis, and pseudomembranous colitis. This discovery may be particularly relevant in patients at risk for enterococcal infections, including vancomycin resistant enterococci (VRE). The present invention has also been discovered to be effective at decreasing the presence of VRE in the gut.

The present invention includes methods for the treatment and prevention of conditions associated with the use of antibiotics without causing or encouraging the growth of vancomycin resistant enterococci (VRE) in the gut. The antibiotic-associated conditions include, but are not limited to, antibiotic-associated diarrhea, colitis, and pseudomembranous colitis.

As it is common for antibiotic associated conditions to recur following treatment with standard antibiotics, the present invention also provides methods for inhibiting relapse of the subject antibiotic-associated conditions in patients. The methods include the administration of ramoplanin in an amount sufficient to inhibit the relapse of antibiotic-associated diarrhea.

Further, as pseudomembranous colitis is especially debilitating, the present invention provides methods for treating pseudomembranous colitis by administering ramoplanin to a patient in need thereof.

The present invention includes relatively short dosing durations for the treatment or prevention of the subject antibiotic associated conditions.

The present invention also provides combination therapies for the treatment and prevention of the subject antibiotic associated conditions. By adding ramoplanin to the standard courses of broad-spectrum antibiotics, the treatments of the present invention prevent the growth of *C. difficile* and other bacteria known to cause antibiotic-associated diarrheal diseases. Antibiotics used in conjunction with ramoplanin in the combination therapies of the present invention include, but are not limited to, vancomycin, bacitracin, and metronidazole. The antibiotics of the combination therapies may be administered sequentially or simultaneously.

The present invention also contemplates compositions and methods for the treatment of symptoms associated with antibiotic associated conditions, which result when antibiotics allow certain bacteria such as toxigenic strains of *C. difficile, S. aureus*, and *C. perfringens* to flourish in the gut. For example, the present invention could include a combination of ramoplanin with an antidiarrheal preparation including, but not limited to, bismuth, diphenoxylate, atropine, kaolin, pectin, loperamide, paragoric, and combinations thereof. In addition, ramoplanin could be combined with preparations to treat the dehydration resulting from chronic diarrhea, including, but not limited to, intravenous fluids or over-the-counter drinks containing electrolytes.

*Clostridium difficile*

*C. difficile* is a Gram-positive anaerobic, spore-forming bacillus, found in the colon of humans. In the 1970's, epidemics of pseudomembranous colitis due to widespread usage of antibiotics were described, and it was discovered that *C. difficile* causes antibiotic associated diarrhea/colitis, and almost all cases of pseudomembranous colitis (Cleary et al., Dis. Colon. Rectum. (1998) 41:1435-1449). These conditions develop as a result of the production of two large toxins, toxin A and toxin B, by *C. difficile* in the colon. Toxin A is a potent enterotoxin and is believed to cause most of the gastrointestinal symptoms. There is also some evidence that toxins A and B act synergistically and that the tissue damage caused by toxin A further potentiates toxin B.

Once infection by *C. difficile* is established, the combined effects of toxin A and toxin B initiate an inflammatory response in the colonic mucosa. The early response is erythema of the mucosa, which resembles other nonspecific colitis syndromes. Symptomatically, the patient experiences abdominal cramps/pain, tenesmus, urgency, diarrhea (including bloody diarrhea) and fever among other symptoms. Progression of the disease results in areas of full mucosal cell death and the appearance of pseudomembranes, which may involve the entire length of the colon. Dilatation of colon, perforation, peritonitis, sepsis, and even death may result.

*C. difficile* is refractory to a number of antimicrobial agents, and is often endemic in hospitals and nursing homes and causes epidemics of the subject conditions. It can appear when the normal bacterial flora in the colon is suppressed, e.g., after treatment with broad-spectrum antibacterial agents. Prolonged nasogastric tube insertion and gastrointestinal tract surgery also increase the risk of developing an infection by *C. difficile*. The overuse of antibiotics, especially penicillin, ampicillin, clindamycin, and cephalosporins alter the normal intestinal flora and increase the risk of developing *C. difficile* infections.

Individuals with *C. difficile*-associated disease shed spores in the stool that can be spread from person to person. Those spores can survive up to 70 days outside a host and can be transported on the hands of health care personnel who have direct contact with infected patients, or they may persist on environmental surfaces.

The pathophysiology of CDAD is not completely understood. It is believed that spores of *C. difficile* are ingested into the upper digestive tract and survive the hostile gastric environment. If the normal bacterial flora has been altered by, for example, systemic antibiotic therapy, the spores can undergo vegetative transformation in the distal small intestine. The *C. difficile* bacteria adhere to the gut mucosal cells, which allows for the proliferation of the organism and production of cytotoxins. Bacteria that fail to adhere to the gut pass harmlessly into the intestinal tract.

Age appears to be a specific risk factor for *C. difficile* enterocolitis, as 80% of the cases appear in patients 65 or older. Other patients at risk include postoperative patients, patients undergoing chemotherapy, patients with bone marrow transplants, and patients suffering from immunological conditions that reduce the effectiveness of the immune system. These immunological conditions may include, but are not limited to, cancer, malnutrition, infection with human immunodeficiency virus, and connective tissue disorders (e.g., lupus erythematosus, Sjögren's Syndrome). Furthermore, these patients are also at risk for VRE colonization and infection (Fry, Pharmanual: Emerging Pathogens and Implications for the Future (1999) pp. 50-75).

Thus, these populations may also benefit from the methods of treatment and compositions described herein.

*Clostridium perfringens*

*C. perfringens* is an anaerobic, Gram-positive, spore forming bacterium. It is widely distributed in the environment and frequently occurs in the intestines of humans and many domestic and feral animals. Spores of the organism persist in soil, sediments, and areas subject to human or animal fecal pollution. *C. perfringens* may cause food poisoning characterized by intense abdominal cramps and diarrhea that begin 8-22 hours after ingestion of enterotoxigenic strains of *C. perfringens*. Death may result due to dehydration and other complications.

*C. perfringens* can also case a far more serious condition known as necrotic enteritis, also known as pig-bel syndrome. This condition is often fatal. The disease begins as a result of ingesting large numbers of *C. perfringens* in contaminated foods. Deaths from necrotic enteritis are caused by infection and necrosis of the intestines and from resulting septicemia.

Institutional feeding (such as school cafeterias, hospitals, nursing homes and prisons) where large quantities of food are prepared several hours before serving is the most common circumstance in which *C. perfringens* food poisoning occurs. The young and elderly are the most frequently affected. Elderly persons are more likely to experience prolonged or severe symptoms.

*C. perfringens* may also cause antibiotic-associated diarrhea similar to that caused by *C. difficile*.

*Staphylococcus aureus*

*S. aureus* is a Gram-positive coccus. Although it is a well-known cause of food poisoning, it may also cause antibiotic-associated diarrhea similar to that caused by *C. difficile*. Staphylococcal enterocolitis may involve the terminal ileum and cecum more frequently than other causes of antibiotic-associated diarrhea, and has usually occurred in the setting of tetracycline and chloramphenicol administration.

Ramoplanin

Ramoplanin (A-16686; MDL 62,198; IB-777), a glycolipodepsipeptide antibiotic obtained from fermentation of Actinoplanes strain ATCC 33076, has targeted activity against Gram-positive aerobic and anaerobic microorganisms. Ramoplanin is described in U.S. Pat. No. 4,303,646, along with the process of manufacture.

Ramoplanin binds to lipid II at a unique site and affects both extracellular and intracellular peptidoglycan synthesis. It has been shown to inhibit the synthesis of the bacterial cell wall by inhibiting the N-acetylglucosaminyl transferase-catalyzed conversion of lipid intermediate I to lipid intermediate II, thus interfering with peptidoglycan synthesis at this step. The mechanism of action of ramoplanin is different from that of vancomycin, teicoplanin, or other cell wall-synthesis inhibitors. No evidence of cross-resistance between ramoplanin and other glycopeptides has been observed.

Ramoplanin's spectrum of activity includes staphylococci, streptococci, clostridia, enterococci, including antibiotic-resistant strains of these species (e.g., methicillin-resistant staphylococci and vancomycin- and gentamicin-resistant enterococci and vancomycin or metronidazole resistant clostridia). Ramoplanin is bactericidal with minimal differences between the minimum inhibitory concentration (MIC) and minimum bactericidal concentration (MBC) for most Gram-positive species.

Ramoplanin has the advantage of being orally administered but not orally absorbed. Thus, a high concentration of orally administered ramoplanin reaches the full length of the gastrointestinal tract, including areas where bacteria such as *C. difficile* are present. Ramoplanin is bactericidal against clinically important Gram-positive bacteria including Enterococcus and Clostridium species. Furthermore, ramoplanin has activity against clostridium species, including *C. difficile* and *C. perfringens*, two organisms associated with diarrhea. In humans, ramoplanin is also known to reduce *S. aureus* colonization in the gut.

Dosages

Ramoplanin is administered orally in an amount and for a duration sufficient to treat CDAD, pseudomembranous colitis, or other diseases associated with the use of antibiotics. Although the exact dosage of ramoplanin sufficient to treat a particular patient may differ, the dosage can be easily determined by a person of ordinary skill. Typically, the amount of ramoplanin that is administered is an amount that maintains the stool concentration of the antibiotic at least equal to the MIC for the target organism. Preferably, the amount of ramoplanin that is administered maintains the stool concentration equivalent to two, three, four, or more times the MIC for the target organism. Thus, the particular treatment regimen may vary for each patient, dependent upon the species and resistance pattern of the identified Gram-positive bacteria, and biological factors unique to each patient including the comorbidity, disease etiology, patient age (pediatric, adult, geriatric), and the nutritional and immune status.

The suggested oral dosage of ramoplanin is at least about 50, 100, 200, 300, 400, or 500 mg/day up to as much as 600, 700, 800, 900, or 1000 mg/day for three to fifteen days. Ramoplanin may be given daily (e.g., once, twice, three times, or four times daily) or less frequently (e.g., once every other day, or once or twice weekly). A particularly suitable dose is between 200 and 400 mg BID (twice daily). The antibiotic may be contained in any appropriate amount in any suitable carrier substance, and is generally present in an amount of 1-99% by weight of the total weight of the composition. The composition is provided in a dosage form that is suitable for oral administration and delivers a therapeutically effective amount of the antibiotic to the small and large intestine, as described below.

Ramoplanin is available as granules for oral solution, provided, for example, in packets containing 400 mg free base of ramoplanin, along with pharmaceutically acceptable excipients (e.g., mannitol, hydroxypropyl methylcellulose, magnesium stearate). The contents of the packet can be reconstituted with approximately 15-30 mL of water, and the resulting solution either consumed directly, or further diluted with water, cranberry juice, apple juice, or 7-Up prior to drinking. After consumption, the drug may be followed with subsequent amounts of these beverages or with food (e.g., cracker, bread). The 400 mg granulated powder packets are stable for at least one year at refrigerated or unrefrigerated conditions. The reconstituted ramoplanin aqueous solution has a shelf life of 48 hours when stored at refrigerated conditions.

Alternatively, ramoplanin is also available as capsules containing pharmaceutically acceptable excipients that are generally regarded as safe. The capsule formulation may be available as 100 mg, 200 mg or 400 mg strengths and are stable for at least one year.

The dosing regimen required to treat CDAD, pseudomembranous colitis, or other disease associated with the use of antibiotics may be altered during the course of the therapy. For example, the patient can be monitored periodically or at regular intervals to measure the patient's bacterial load and dosage or frequency of antibiotic therapy can be adjusted accordingly. Ramoplanin may be dosed for a duration shorter or similar to that of commonly used treatments.

Pharmaceutical Formulations

Pharmaceutical compositions according to the invention may be formulated to release an antibiotic substantially immediately upon administration or at any predetermined time or time period after administration. The latter types of compositions are generally known as controlled release formulations, which include formulations that create a substantially constant concentration of the drug within the intestinal tract over an extended period of time, and formulations that have modified release characteristics based on temporal or environmental criteria.

Any oral biologically-acceptable dosage form, or combinations thereof, can be employed in the methods of the invention. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, ingestibles, infusions, health bars, confections, animal feeds, cereals, cereal coatings, foods, nutritive foods, functional foods and combinations thereof. The preparation of any of the above dosage forms is well known to persons of ordinary skill in the art. Additionally, the pharmaceutical formulations may be designed to provide either immediate or controlled release of the antibiotic upon reaching the target site. The selection of immediate or controlled release compositions depends upon a variety of factors including the species and antibiotic susceptibility of Gram-positive bacteria being treated and the bacteriostatic/bactericidal characteristics of the therapeutics. Methods well known in the art for making formulations are found, for example, in Remington: The Science and Practice of Pharmacy (20th ed.), ed. A. R. Gennaro, 2000, Lippincott Williams & Wilkins, Philadelphia, or in Encyclopedia of Pharmaceutical Technology, eds. J. Swarbrick and J. C. Boylan, 1988-1999, Marcel Dekker, New York.

Immediate release formulations for oral use include tablets or capsules containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, mannitol, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the antibiotic with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice. Other useful controlled release compositions are known in the art (see, for example, U.S. Pat. Nos. 4,946,685 and 6,261,601).

Formulations that target ramoplanin release to particular regions of the intestinal tract can also be prepared. Ramoplanin can be encapsulated in an enteric coating that prevents release degradation and release from occurring in the stomach, but dissolves readily in the mildly acidic or neutral pH environment of the small intestine. A formulation targeted for release of antibiotic to the colon, utilizing technologies such as time-dependent, pH-dependent, or enzymatic erosion of polymer matrix or coating can also be used.

Alternatively, a multilayer formulation having different release characteristics between the layers can be prepared. These formulations can result in the antibiotic being released in different regions of the intestinal tract. A multilayer formulation of this type may be particularly useful for maintaining a more constant antibiotic concentration throughout the length of the intestinal tract.

The targeted delivery properties of the ramoplanin-containing formulation may be modified by other means. For example, the antibiotic may be complexed by inclusion, ionic association, hydrogen bonding, hydrophobic bonding, or covalent bonding. In addition polymers or complexes susceptible to enzymatic or microbial lysis may also be used as a means to deliver drug.

Microsphere encapsulation of ramoplanin is another useful pharmaceutical formulation for targeted antibiotic release. The antibiotic-containing microspheres can be used alone for antibiotic delivery, or as one component of a two-stage release formulation. Suitable staged release formulations may consist of acid stable microspheres, encapsulating ramoplanin to be released later in the lower intestinal tract admixed with an immediate release formulation to deliver antibiotic to the stomach and upper duodenum.

Microspheres can be made by any appropriate method, or from any pharmaceutically acceptable material. Particularly useful are proteinoid microspheres (see, for example, U.S. Pat. Nos. 5,601,846, or 5,792,451) and PLGA-containing microspheres (see, for example, U.S. Pat. Nos. 6,235,224 or 5,672,659). Other polymers commonly used in the formation of microspheres include, for example, poly-ε-caprolactone, poly(ε-caprolactone-Co-DL-lactic acid), poly(DL-lactic acid), poly(DL-lactic acid-Co-glycolic acid) and poly(ε-caprolactone-Co-glycolic acid) (see, for example, Pitt et al., J. Pharm. Sci., 68:1534, 1979). Microspheres can be made by procedures well known in the art including spray drying, coacervation, and emulsification (see for example Davis et al. Microsphere and Drug Therapy, 1984, Elsevier; Benoit et al. Biodegradable Microspheres: Advances in Production Technologies, Chapter 3, ed. Benita, S, 1996, Dekker, N.Y.; Microencapsulation and Related Drug Processes, Ed. Deasy, 1984, Dekker, N.Y.; U.S. Pat. No. 6,365,187).

Powders, dispersible powders, or granules suitable for preparation of aqueous solutions or suspensions of ramoplanin by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

EXAMPLE 1

Efficacy of Ramoplanin in the Hamster Model of C. difficile Associated Colitis

To evaluate the in vivo efficacy of ramoplanin in the treatment of C. difficile-associated colitis, ramoplanin was tested in a hamster model of clindamycin (CL)-induced colitis in comparison with both vancomycin and metronidazole. Animals were treated with a single subcutaneous (s.c.) injection of 100 mg/kg clindamycin, and after 24 hours received oral ramoplanin or vancomycin at 50 mg/kg/day for 5 days. Animals were observed daily for the presence or absence of diarrhea. Necropsies were performed on some animals that died during the experiment, and cecal contents were assayed for C. difficile toxin A. Hamsters were monitored for 20 days, and the cumulative mortality during this period was recorded (FIG. 1). Clindamycin alone rapidly induced a fatal enterocolitis with 100% mortality within 4 days. Autopsy revealed hemorrhagic ceca and watery stools. C. difficile toxin A was always detected in these animals. Oral administration of either vancomycin or ramoplanin was highly effective in prolonging survival and protecting animals from death (FIG. 1). Ramoplanin was significantly more effective than vancomycin, with an 80% survival rate compared to 20% for vancomycin-treated animals (P<0.05). All hamsters that died had gross pathologic evidence of enterocolitis and cecal contents were positive for Toxin A.

Figure 2:
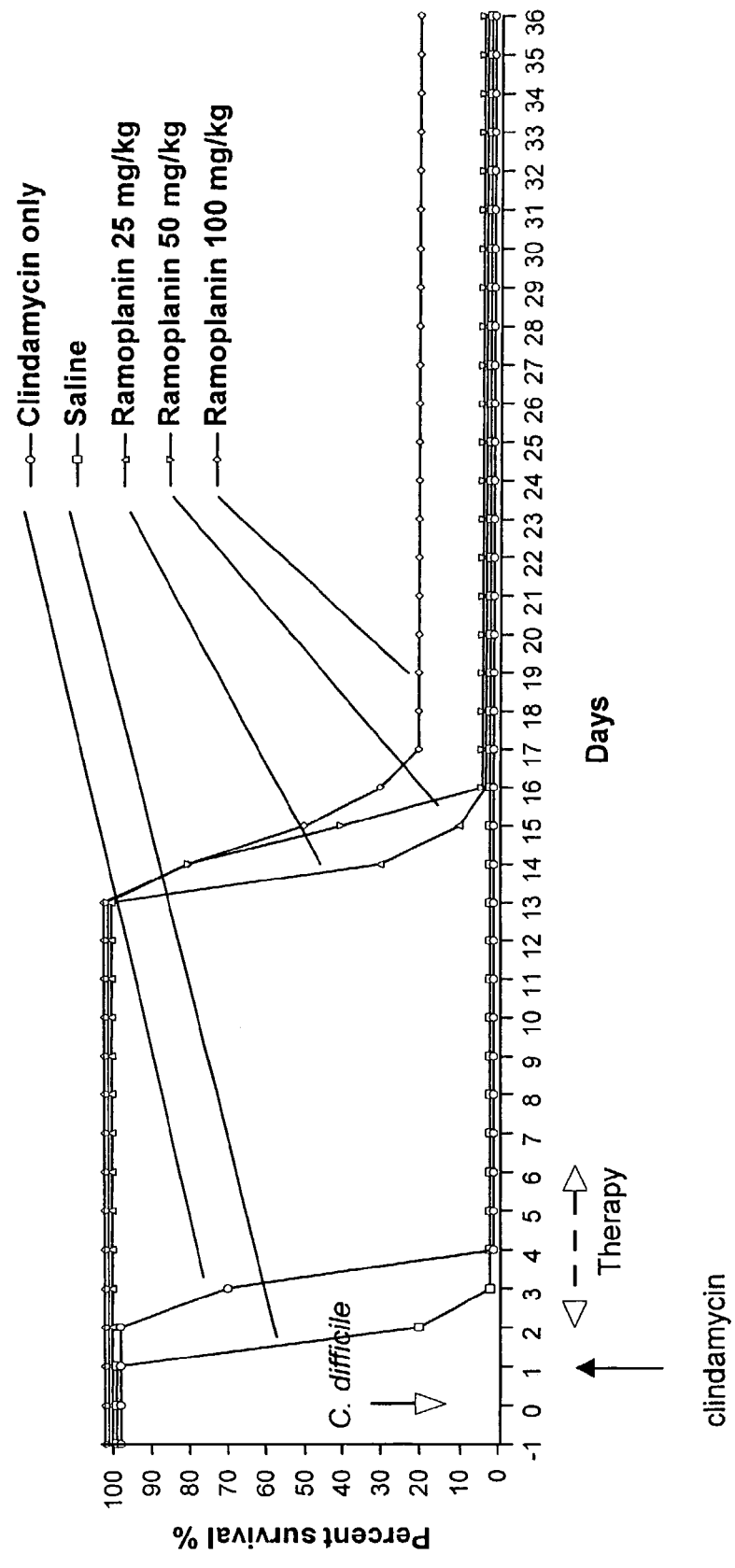
FIG. 2 is a graph showing the effect of ramoplanin on CDAD induced in Syrian hamsters by adminstration of clindamycin and *C. difficile* strain 4013.
Figure 3:
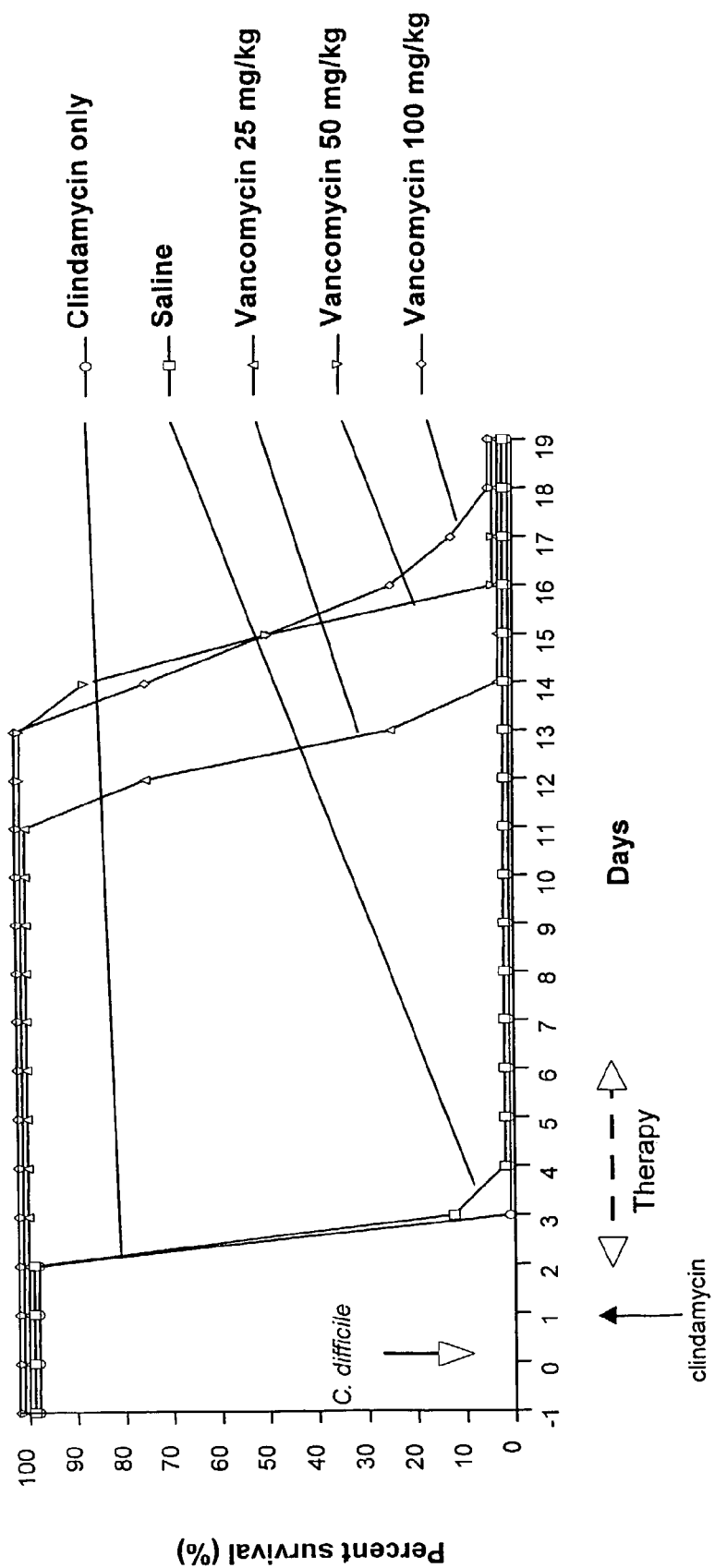
FIG. 3 is a graph showing the effect of vancomycin on CDAD induced in Syrian hamsters by adminstration of clindamycin and *C. difficile* strain 4013.
Figure 4:
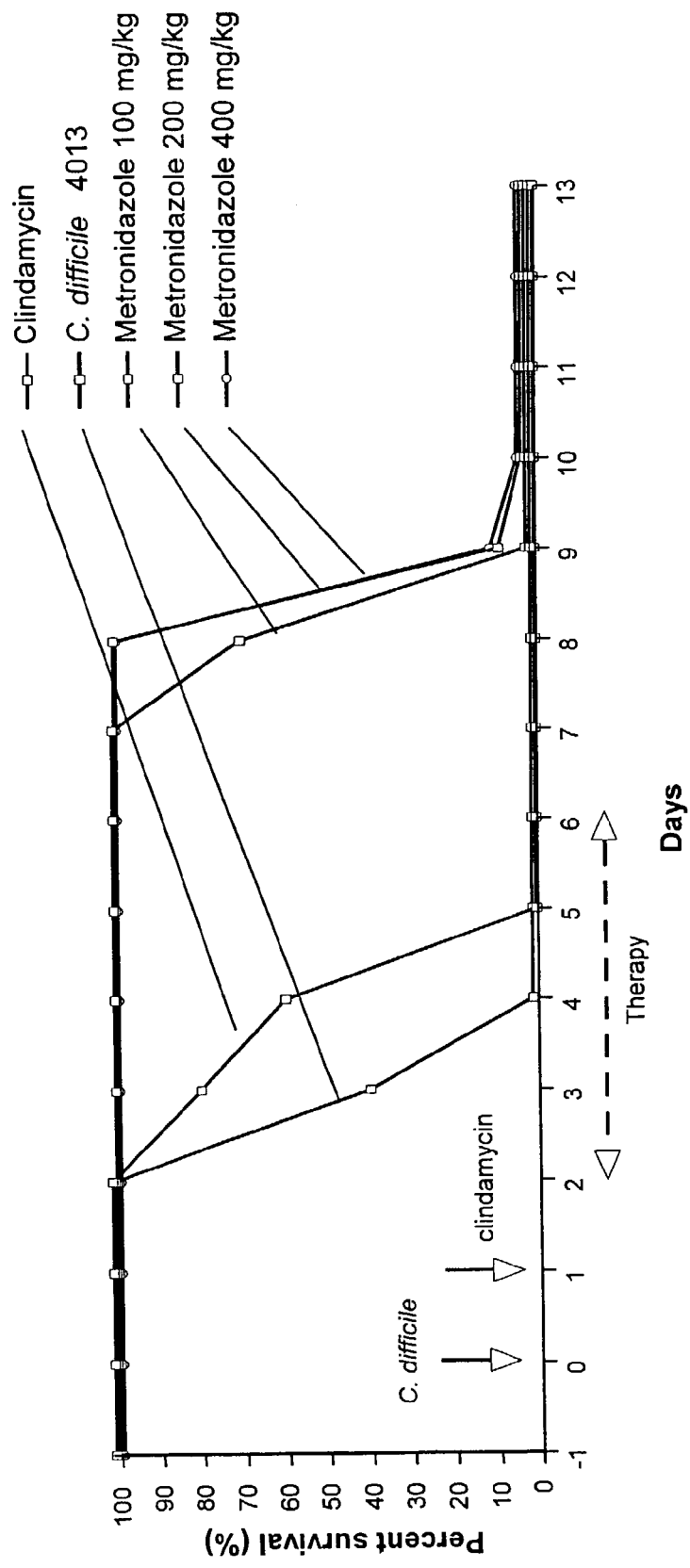
FIG. 4 is a graph showing the effect of metronidazole on CDAD induced in Syrian hamsters by adminstration of clindamycin and *C. difficile* strain 4013.

In a second study, animals were challenged orally with a bacterial suspension of C. difficile and then administered a single s.c. injection of 100 mg/kg clindamycin. Oral treatment with ramoplanin or vancomycin at 25-50-100 mg/kg or metronidazole at 100-200-400 mg/kg started 24 hours after clindamycin administration and lasted for five days. Hamsters were weighed and observed every 24 hours for evidence of diarrhea or moribund conditions, and the cecal contents were analyzed for C. difficile toxin A (ELISA). The challenge with C. difficile to clindamycin-treated animals also induced a rapidly fatal enterocolitis (FIGS. 2-4). Both vancomycin and ramoplanin were more effective in prolonging survival than was metronidazole (13-17 days and 9 days respectively). Time of death in ramoplanin-treated animals was delayed compared to that of vancomycin-treated animals, and 20% survival was recorded at the end of observation period in the group treated with 100 mg/kg ramoplanin (FIG. 2). No animals treated with vancomycin or metronidazole survived the study (FIGS. 3 and 4).

Figure 5:
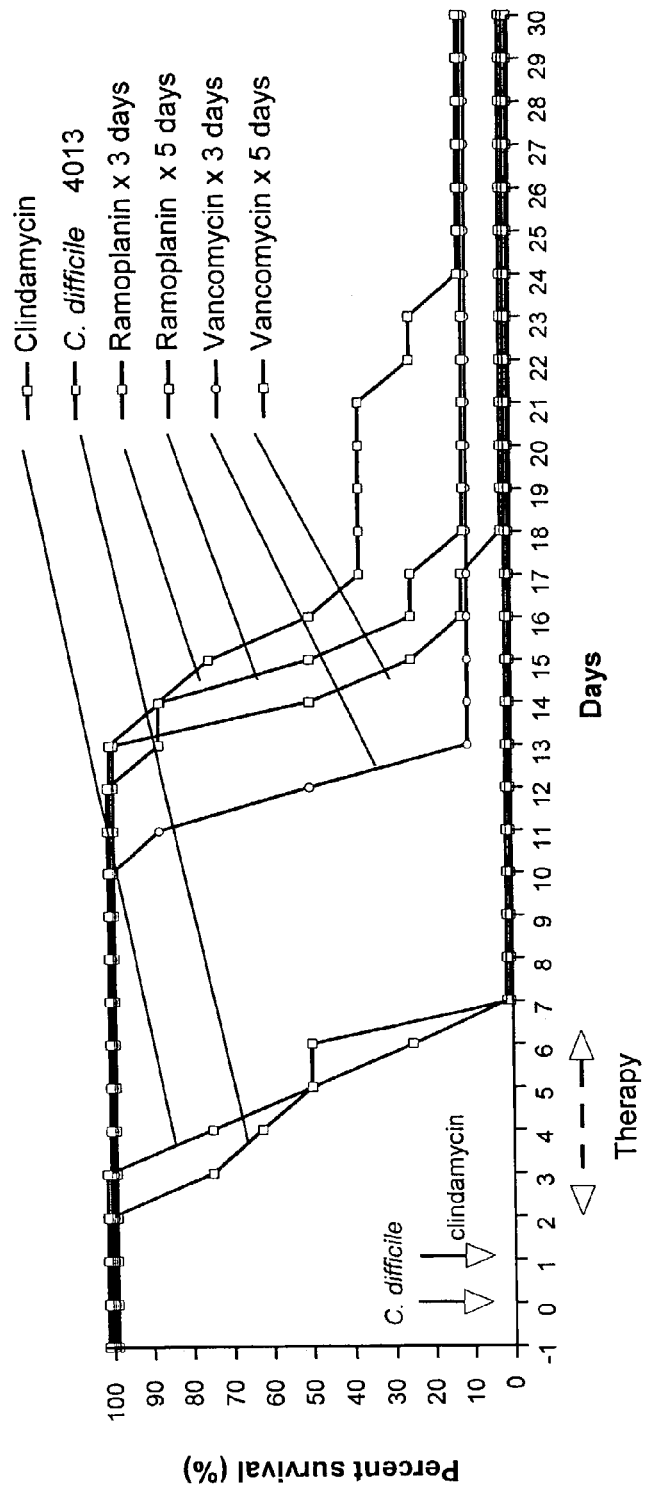
FIG. 5 is a graph showing the effect of various durations of treatment with ramoplanin or vancomycin on CDAD induced in Syrian hamsters by adminstration of clindamycin and *C. difficile* strain 4013.

The effect of different durations of treatment with ramoplanin or vancomycin is shown in FIG. 5. Hamsters were inoculated with C. difficile on day 0 and then administered 100 mg/kg clindamycin s.c. on day 1. Hamsters received daily oral doses of 50 mg/kg ramoplanin or vancomycin for 3 or 5 days starting on day 2. Ramoplanin administration for 3 days was more effective than vancomycin administration for 5 days (FIG. 5).

In another study, animals were administered a single dose of clindamycin and then treated with either vancomycin or ramoplanin. C. difficile spores were recovered from some of the animals treated with vancomycin. No C. difficile spores or vegetative cells were recovered from any animals treated with ramoplanin.

EXAMPLE 2

Oral Administration of Ramoplanin to Humans

As is described in detail below, single oral doses (up to 1000 mg) and multiple oral doses (200, 400, or 800 mg BID for 10 days) of ramoplanin have been administered to healthy male volunteers. Both bioassay and HPLC-based assays to assess the absorption, distribution, metabolism, and excretion were utilized in these studies. Ramoplanin was not detected in serum/plasma or urine by either method, indicating that very little, if any, is absorbed. Treatment with oral ramoplanin at all doses was efficacious in reducing the Gram-positive colony counts in feces to undetectable levels during the 10-day regimen. Ramoplanin was not effective against Gram-negative flora.

Single Dose Study in Healthy Male Volunteers

The absorption, tolerability, and recovery of ramoplanin following single dose oral administration were investigated in male volunteers. Ramoplanin was administered as an aqueous solution at a dose of 100, 200, 500, or 1000 mg to fasting subjects. Serum samples were obtained prior to drug administration of ramoplanin and 0.5, 1, 2, 3, 6, 9, 12, 24, 48, 72, and 96 hours after treatment. Urine samples were collected prior to administration of ramoplanin and over the periods 0-3,3-6, 6-12, 12-24, 24-48, 48-72, and 72-96 hours after dosing. Fecal samples were collected prior to dosing and over the periods 0-16 (Day 1), 16-40 (Day 2), 40-64 (Day 3), 64-88 (Day 4), and 88-96 (Day 5) hours after dosing. A microbiological assay employing Bacillis subtilis ATCC 6633 as the test organism was used to determine ramoplanin concentrations in serum, urine, and feces. The limits of quantitation for this assay were 0.02 μg/mL in serum, 0.012 μg/mL in urine, and 3 μg/g in feces. Tolerability was assessed on the basis of clinical signs and symptoms and the results of blood and urine laboratory tests.

Ramoplanin concentrations in feces varied widely due to the variation in the weight of the fecal samples (6-468 g); detectable concentrations ranged from 2.9 to 278 μg/g in the 100 mg group, 7.7 to 454 μg/g in the 200 mg group, 6.6 to 3316 μg/g in the 500 mg group, and 16.0 to 3154 μg/g in the 1000 mg group. Maximum ramoplanin concentrations in feces, as well as maximum percentage recoveries, generally occurred the day after administration (Day 2). The time of occurrence of maximum ramoplanin concentrations in feces was not dose dependent. In contrast, the maximum ramoplanin fecal concentrations were dose-dependent. Mean maximum concentrations were 214 μg/g (range 148-278 μg/g), 287 μg/g (range 164-454 μg/g), 1655 μg/g (range 737-3316

μg/g), and 1835 μg/g (range 1336-3154 μg/g) for the 100, 200, 500, and 1000 mg groups, respectively. Mean cumulative recovery of ramoplanin in feces for the 100, 200, 500, and 1000 mg groups were 67.7% (range 55.7-84%), 48.5% (range 39.3-56.5%), 52.8% (range 41.3-79.6%), and 46.4% (range 39.9-58.4%) of the administered dose, respectively. On the fourth day of study, ramoplanin was still detectable in feces obtained from 17 of 24 subjects.

Multiple Dose Study in Healthy Male Volunteers

Healthy male volunteers were administered 200, 400, or 800 mg ramoplanin twice-a-day, for ten consecutive days. The predetermined dose was reconstituted in 5 mL water per vial, mixed with 50 mL of sweetened, aromatized solution, and immediately administered orally to the subjects.

No absorption from the human gastrointestinal tract was observed. On Days 1, 5, and 10, no serum levels of ramoplanin were detected at hour 0.5, 1, 2, 3, 6, 9, and 12 after the morning dose. No levels were found in urine at Day 1 and 5, or in the pooled urine samples of the periods 0-12, 12-24, 24-36, 48-72, and 72-96 after the last dose.

The fecal concentrations of ramoplanin were dose related on both Day 3 (average concentration 827, 1742, 1901 μg/g in the 200, 400, and 800 mg group, respectively) and Day 10 (949, 1417, 2647 μg/g, respectively). The concentrations declined on the first day post-treatment, but remained detectable in some subjects four days post-treatment. The cumulative recovery up to Day 4 post-treatment was 25% of the administered dose.

The antibacterial activity of ramoplanin on the stool microflora was assessed in a subset of the subjects. Microbial concentrations (i.e., the number of organisms per gram of fecal matter) were determined at the following time points: Day −4 (pre-treatment), Days 4 and 10 (treatment), and Days 7 and 24 (follow-up). Tolerability and absorption were also investigated.

As expected, no effect was seen in Gram-negative bacteria (enteric bacteria and *Bacteroides* spp.) or yeast. A marked effect was seen on Gram-positive bacteria by the first measurement on Day 4. In all subjects, the concentrations of staphylococci, streptococci, and enterococci were below the level of detection by Day 10. In 10 of 12 subjects, the concentration of ramoplanin and vancomycin-resistant *Clostridium* spp. was reduced below detectable levels. In the other two subjects who carried ramoplanin- and vancomycin-resistant *Clostridium* spp. (*C. rectum* and *C. bejerinckii*) before treatment, no variation in the clostridial load was observed. No ramoplanin- or vancomycin-resistant strain of *C. difficile* was detected, either pre- or post-treatment.

After therapy, the intestinal tracts of the volunteers were re-colonized by normal Gram-positive bacteria, with a tendency for enterococci and clostridia to transiently achieve concentrations higher than the basal level. To evaluate if the predominant species that colonized the intestinal tract after therapy was that isolated before treatment, all enterococci isolated before and after ramoplanin therapy were speciated using the API system. DNA-typing was also performed when identification at the strain level was necessary. In most cases, the predominant strain appeared to be different before and after treatment, suggesting a lack of persistence of the initial isolate.

The in vitro interaction of ramoplanin with human intestinal contents was studied. Ramoplanin was found to be microbiologically active in feces and to bind reversibly to solid components of feces. The binding and the subsequent release of ramoplanin from feces would likely result in long-lasting concentrations in the intestinal tract.

Multiple Dose Study in Asymptomatic Carriers of Intestinal VRE

Patients identified as asymptomatic carriers of VRE were administered placebo or one of two dosages (100 mg, 400 mg) of ramoplanin BID (twice daily) for seven days. Patients were assessed by rectal swab on Days 7, 14, and 21 to determine the presence or absence of VRE. On Days 45 and 90, stool samples were analyzed for long-term effects of ramoplanin on the recurrence of, or reinfection with, VRE. All VRE isolates were tested for susceptibility to ramoplanin.

Analysis of the primary efficacy variable showed that ramoplanin effectively suppressed intestinal VRE (i.e., ramoplanin substantially decolonized the intestinal tract of VRE). None of the placebo-treated patients were VRE-free after seven days of treatment. In contrast, 17 of 21 patients (81.0%; $p<0.01$) who received 100 mg ramoplanin BID and 18 of 20 patients (90.0%; $p<0.01$) who received 400 mg ramoplanin BID were had no detectable VRE at Day 7. Seven days after cessation of treatment (Day 14), 6 of 21 patients (28.6%) who received 100 mg ramoplanin BID and 7 of 17 patients (41.2%) who received 400 mg ramoplanin BID remained VRE free. At Day 21, the number of VRE-free patients was comparable among all treatment groups.

Other Embodiments

All references discussed above are herein incorporated by reference in their entirety for all purposes. While this invention has been particularly shown and described with references to preferred embodiments thereof, it will be understood by those skilled in the art that various changes in form and details may be made therein without departing from the spirit and scope of the invention as defined by the appended claims.

What we claim is:

1. A method of treating a patient with a *Clostridium difficile*-associated condition, said method comprising administering to said patient ramoplanin in an amount and for a duration effective to treat said condition, wherein said method is effective for reducing the population of *Clostridium difficile* and *Clostridium difficile* spores.

2. The method of claim 1, wherein said *Clostridium difficile* is resistant to metronidazole and/or vancomycin.

3. The method of claim 1, wherein said *Clostridium difficile*-associated condition is selected from the group consisting of antibiotic-associated diarrhea, colitis, and pseudomembranous colitis.

4. The method of claim 1, wherein said ramoplanin is administered in an amount between 50 mg and 1 g.

5. The method of claim 4, wherein said ramoplanin is administered in an amount between 200 and 400 mg once or twice daily.

6. The method of claim 1, wherein said ramoplanin is administered one to four times daily for three to fifteen days.

7. The method of claim 1, wherein said ramoplanin is administered orally.

8. The method of claim 1, further comprising administering to said patient vancomycin, bacitracin, or metronidazole.

* * * * *